(12) United States Patent
Gordon et al.

(10) Patent No.: US 9,943,677 B2
(45) Date of Patent: Apr. 17, 2018

(54) SECURING A MEDICAL DEVICE TO A VALVE INSTRUMENT

(71) Applicant: Radux Devices, LLC, Omaha, NE (US)

(72) Inventors: Gregory Gordon, Omaha, NE (US); Ryan Balko, Maple Grove, MN (US); Anders Olmanson, Eagan, MN (US); Travis White, Zimmerman, MN (US)

(73) Assignee: Radux Devices, LLC, Omaha, NE (US)

( * ) Notice: Subject to any disclaimer, the term of this patent is extended or adjusted under 35 U.S.C. 154(b) by 469 days.

(21) Appl. No.: 14/514,815

(22) Filed: Oct. 15, 2014

(65) Prior Publication Data

US 2015/0105752 A1  Apr. 16, 2015

Related U.S. Application Data (60) Provisional application No. 61/891,312, filed on Oct. 15, 2013.

(51) Int. Cl.
*A61M 39/06* (2006.01)

(52) U.S. Cl.
CPC ... *A61M 39/0693* (2013.01); *A61M 2039/062* (2013.01); *A61M 2039/064* (2013.01)

(58) Field of Classification Search
CPC ........ A61M 39/0693; A61M 2039/062; A61M 2039/0626; A61M 2039/064
See application file for complete search history.

(56) References Cited

U.S. PATENT DOCUMENTS

| 3,853,126 | A |   | 12/1974 | Schulte |
|---|---|---|---|---|
| 3,998,222 | A |   | 12/1976 | Shihata |
| 4,316,461 | A |   | 2/1982 | Marais et al. |
| 4,387,879 | A | * | 6/1983 | Tauschinski ........ A61M 39/045 137/846 |
| 4,453,933 | A |   | 6/1984 | Speaker |
| 4,850,954 | A |   | 7/1989 | Charvin |
| 4,865,586 | A |   | 9/1989 | Hedberg |
| 4,976,698 | A |   | 12/1990 | Stokley |
| 5,031,775 | A |   | 7/1991 | Kane |
| 4,840,613 | B1 |   | 7/1993 | Balbierz |
| 5,443,460 | A |   | 8/1995 | Miklusek |
| 5,538,513 | A |   | 7/1996 | Okajima |
| 5,647,859 | A |   | 7/1997 | Lampropoulos et al. |
| 5,693,031 | A | * | 12/1997 | Ryan ................ A61B 17/3496 604/167.03 |
| 5,902,274 | A |   | 5/1999 | Yamamoto et al. |
| 5,916,199 | A |   | 6/1999 | Miles |
| 5,947,931 | A |   | 9/1999 | Bierman |
| 5,989,223 | A |   | 11/1999 | Chu et al. |
| 6,001,081 | A |   | 12/1999 | Collen |
| 6,113,577 | A |   | 9/2000 | Hakky et al. |
| 6,165,168 | A |   | 12/2000 | Russo |

(Continued)

OTHER PUBLICATIONS

International Preliminary Report on Patentability for PCT/2014/060668, dated Apr. 28, 2016, 14 pages.

(Continued)

*Primary Examiner* — Lauren P Farrar
(74) *Attorney, Agent, or Firm* — Fish & Richardson P.C.

(57) ABSTRACT

Apparatus and techniques for securing a medical device with hemostasis valve are described.

29 Claims, 5 Drawing Sheets

(56) References Cited

U.S. PATENT DOCUMENTS

| | | | |
|---|---|---|---|
| 6,287,280 B1* | 9/2001 | Lampropoulos | A61M 39/0693 604/165.01 |
| 7,198,066 B2 | 4/2007 | Kagenow | |
| 7,553,326 B2 | 6/2009 | Sweet | |
| 8,361,020 B2* | 1/2013 | Stout | A61M 25/0693 604/122 |
| 8,911,396 B2 | 12/2014 | Gordon | |
| 2001/0053895 A1 | 12/2001 | Vaillancourt | |
| 2002/0087108 A1 | 7/2002 | Maginot et al. | |
| 2002/0107479 A1 | 8/2002 | Bates et al. | |
| 2004/0024381 A1 | 2/2004 | Kurth et al. | |
| 2004/0087905 A1 | 5/2004 | Breznock et al. | |
| 2004/0153021 A1 | 8/2004 | Osborne et al. | |
| 2005/0043684 A1* | 2/2005 | Basta | A61M 25/01 604/164.13 |
| 2005/0113799 A1 | 5/2005 | Lenker | |
| 2005/0165364 A1 | 7/2005 | DiMatteo | |
| 2005/0209584 A1 | 9/2005 | Rome | |
| 2005/0234405 A1 | 10/2005 | Dikeman et al. | |
| 2006/0009737 A1 | 1/2006 | Whiting et al. | |
| 2006/0047266 A1 | 3/2006 | Elkins et al. | |
| 2006/0074398 A1 | 4/2006 | Whiting et al. | |
| 2006/0084927 A1 | 4/2006 | Formichi | |
| 2006/0129091 A1 | 6/2006 | Bonnette et al. | |
| 2006/0129112 A1 | 6/2006 | Lynn | |
| 2006/0129134 A1 | 6/2006 | Kerr | |
| 2007/0161956 A1 | 7/2007 | Heuser | |
| 2007/0167901 A1 | 7/2007 | Herrig et al. | |
| 2007/0225680 A1 | 9/2007 | Biggins | |
| 2008/0171944 A1 | 7/2008 | Brenneman | |
| 2008/0183183 A1 | 7/2008 | Kida et al. | |
| 2008/0195046 A1 | 8/2008 | Altman | |
| 2008/0262475 A1 | 10/2008 | Preinitz | |
| 2009/0264811 A1* | 10/2009 | Asfora | A61B 5/031 604/28 |
| 2009/0297260 A1 | 12/2009 | Doll et al. | |
| 2009/0306574 A1 | 12/2009 | Kopperschmidt | |
| 2010/0030162 A1 | 2/2010 | Cremascoli et al. | |
| 2012/0130151 A1 | 5/2012 | Kassab et al. | |
| 2012/0259292 A1 | 10/2012 | Koehler | |
| 2013/0006163 A1 | 1/2013 | Gordon | |

OTHER PUBLICATIONS

European Office Action in Application No. 14853360.7, dated Dec. 14, 2016, 5 pages.
International Search Report and Written Opinion for PCT/US2014/060668 dated Jan. 28, 2015, 17 pages.
European Search Report in Application No. 14853360.7, dated Dec. 1, 2016, 4 pages.

* cited by examiner

SECURING A MEDICAL DEVICE TO A VALVE INSTRUMENT

CROSS-REFERENCE TO RELATED APPLICATIONS

This application claims the benefit of U.S. Provisional Application Ser. No. 61/891,312, filed Oct. 15, 2013. The disclosure of the prior application is considered part of (and is incorporated by reference in) the disclosure of this application.

TECHNICAL FIELD

This disclosure relates to securing a medical device (e.g., a catheter or other elongate device) to a valve instrument (e.g., a hemostasis valve or other medical valve device). In particular embodiments, this disclosure relates to apparatus and techniques for securing a medical device and hemostasis valve together.

BACKGROUND

Hemostasis valves are used during some interventional procedures to minimize back bleeding and to prevent the introduction of air that may result in an embolism, while permitting the introduction of medicine and medical devices to blood vessels in a patient's circulatory system. For example, a hemostasis valve can be used to introduce wires, sheaths, catheters which may be equipped with balloons and lumens, and other elongate medical devices into a vein or artery. Example procedures include, but are not limited to, angiography, angioplasty and embolization procedures. In other examples, a hemostasis valve is used during a fluoroscopy procedure to introduce fluoroscopically identifiable materials, e.g., barium dye, to observe the patient's circulatory system. In some circumstances, interior portions of the hemostasis valve can be pressurized with liquid to prevent blood or gases from escaping.

Some hemostasis valves are y-shaped with three ports that are individually associated with an arm of the "y". The ports are configured as input ports for accepting a medical device or a liquid, or as an exit port through which the medical device or liquid passes into the patient's circulatory system. Other commercially available hemostasis valves include additional arms, e.g., a double-y configuration, that has an additional port for introducing a medical device or liquids through the valve and into the patient. Hemostasis valves can include a variety of valve systems to control movement of liquids, medical devices, and so on in the valve. The valve systems typically include a primary valve, such as a three-way stopcock type valve, for a standard hemostasis valve, and a variety of seals or mechanism for controlling addition/removal of medical devices and fluids. One of the ports, for example, an inlet port that is often axially align with the outlet port, can include a "twist-lock" or "push-pull lock" to control introduction of or removal of a medical device from the patient. Some elongate medical devices used with hemostasis valves can be fed or withdrawn by manipulating one of these lock devices to lock or seal the valve and then to insert or withdraw the device to target where the medicine or device is located. For example, an access sheath (having one or more guide wires therein) may be fed through an inlet port into the valve for eventual insertion into a vein.

The sizes of the inlet ports for hemostasis valves vary based on different manufacturers. Thus, although the hemostasis valve can be a particular French size indicating how large the valve is, the internal components (especially the seal devices proximate to the inlet port(s)) can be sized and configured differently between various manufacturers.

SUMMARY

Some embodiments described herein provide a universal adapter tool configured to secure an elongate medical device to an inlet port of a hemostasis valve (or other medical valve device) in a manner that provides an effect seal even when the outer size of the elongate medical device is not matched to the inlet port size of the valve device. In particular embodiments, the adapter tool can be adhered or otherwise engaged to an exterior surface of the elongate medical device so that the adapter tool provides a transition (and a sealed arrangement) between an inner valve component of a hemostasis valve and the exterior surface of the elongate medical device. In such circumstances, the adapter tool permits the elongate medical instrument to be used with a variety of hemostasis valves (or other medical valve devices) beyond the limited types of hemostasis valves that are specifically manufactured to mate with the particular size of the elongate medical instrument.

Some embodiments of an adapter tool described herein include a body portion that has a tapered body portion (e.g, a linear taper for frustroconical shape, a concave curved taper for hyperbolic conical shape, a convex curved taper for a bulbous shape, or the like) and includes one or more protrusions that extend outwardly from the tapered body portion's primary axis to engage an inlet port from any of a range of differently sized inlet ports included on hemostasis valves from different manufacturers. Each protrusion can be shaped as a ring, threading, a segment of a thread, another protruding structure, or a combination. The body portion of the adapter tool can surround a lumen of the adapter tool, which is configured to engage with an exterior surface of an elongate a medical device for passage of the elongate medical device into the hemostasis valve.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENT

Figure 1:
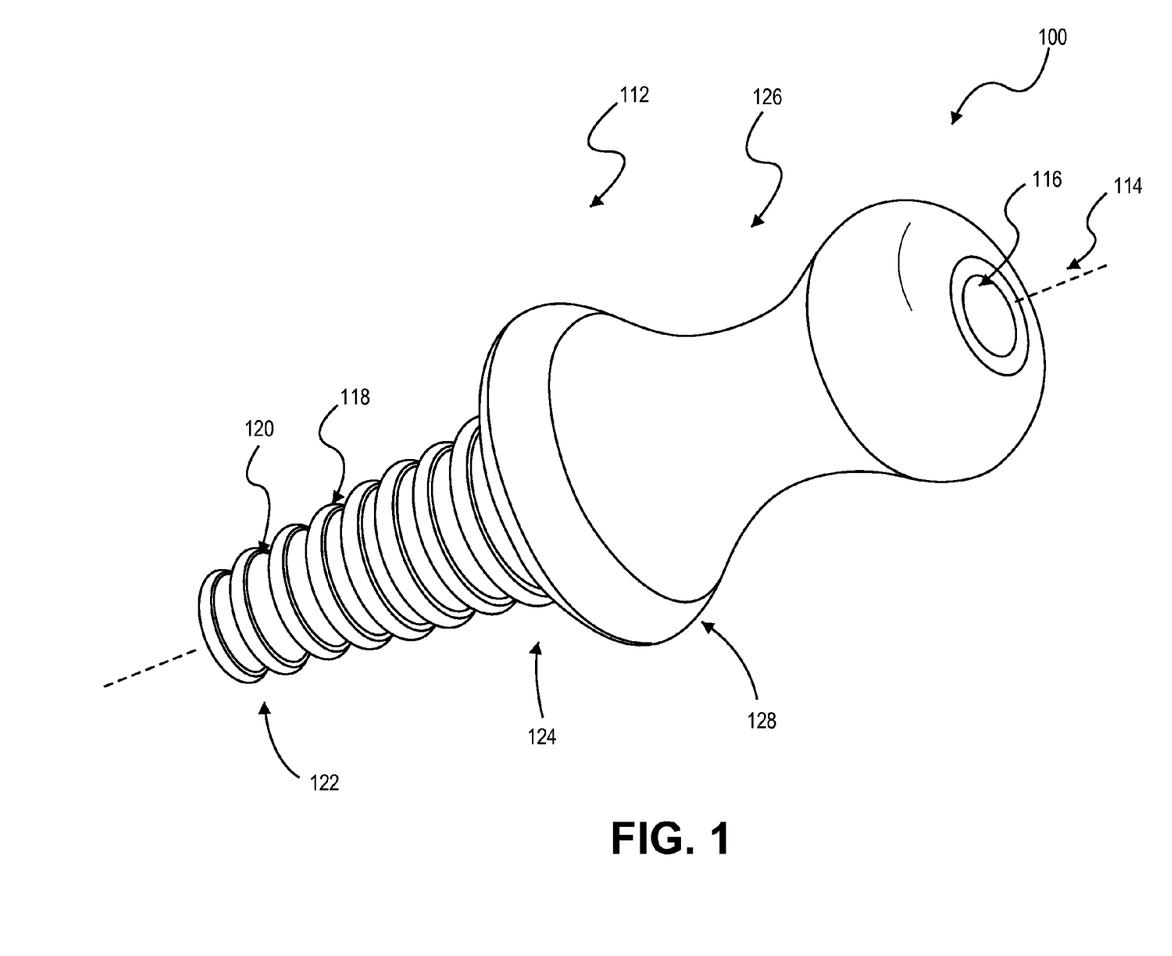
FIG. 1 is a cross-sectional view of a system, including an adapter tool, for securing a medical device to a valve instrument, in accordance with some embodiments.
Figure 2:
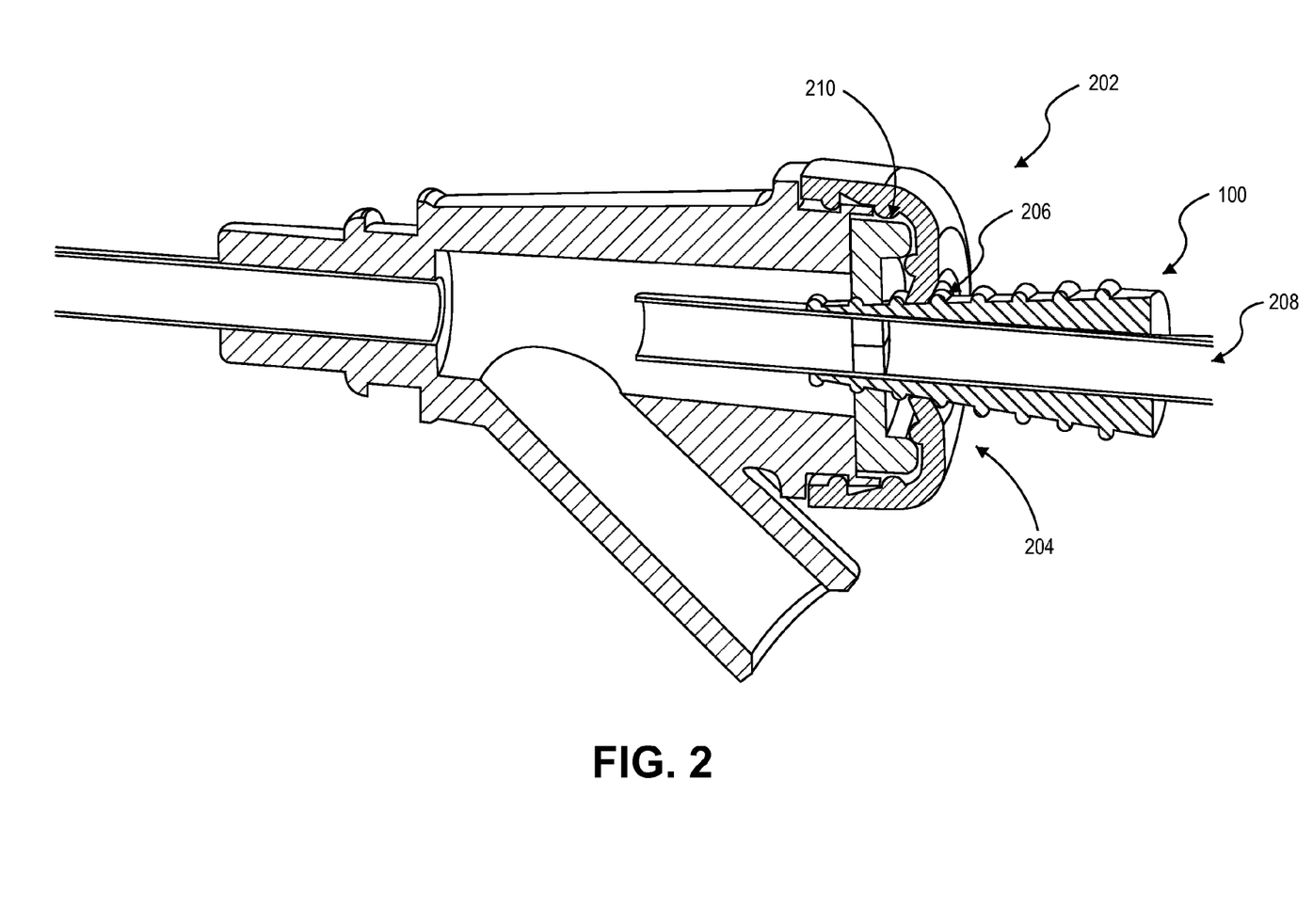
FIG. 2 is perspective view of the adapter tool of FIG. 1, in accordance with some embodiments.

Referring to FIGS. 1-2, some embodiments of a medical device securement system 50 include an adapter tool 100 configured to secure an elongate medical device 220 to an inlet port 202 of a medical valve device 200 (a hemostasis valve device in this embodiment). The adapter tool 100 has a number of structural feature that cooperate to engage with elongate medical device 220 while also providing an effective seal with a valve component 210 even when the outer size of the elongate medical device 220 is not matched to the inlet port size of the valve device 200. As described in more detail below, the adapter tool 100 can be optionally adhered or otherwise engaged to an exterior surface 222 of the elongate medical device 220 so that the adapter tool 100 provides a transition between the inner valve component 210 of the hemostasis valve device 200 and the exterior surface 222 of the elongate medical device 220. Moreover, in this embodiment, a distal body portion 112 of the adapter tool 100 can have a tapered shaped, thereby providing a outer dimension for engaging with the inner valve component 210 that progressively increases as the insertion depth of the adapter tool 100 increases. In such circumstances, the adapter tool 100 can serve as a useful, universal adapter that permits the elongate medical device 220 to be used with a variety of hemostasis valve devices even when the hemostasis valve device 200 is not specifically manufactured to mate with the particular size of the elongate medical device 220.

The hemostasis valve device 200 used with the adapter tool 100 can be implemented from any of a variety of proprietary designs based on the manufacturer of the valve device 200. For example, manufacturers often produce hemostasis valve devices with differently sized inlet ports for accepting differently sized access sheaths (or other medical devices) for interventional procedures. In this example, the inlet port 202 may include a deformable seal component 210 with an opening that is configured to sealingly engage with an exterior surface of the access sheath passing through it. In some embodiments, the hemostasis valve may include multiple seal components (element 210 or having a different configuration) to ensure fluid does not escape while the sheath is inserted or removed.

As previously described, the inlet ports of various hemostasis valves can differ in size and configuration between various manufacturers, which can lead to circumstances in which the access sheath 220 (or other elongate medical device) to be used by a practitioner at a hospitals, clinic, or radiological imaging center is not sized to perfectly mate with the inlet port 202 of the selected hemostasis valve device 200. In some embodiments, the adapter tool 100 can be beneficial used in those circumstances for securing the access sheath 220 to the inlet port 202 of the selected hemostasis valve device 200.

Still referring to FIGS. 1-2, particular embodiments of the adapter tool 100 can be adhered or otherwise mounted to the exterior of the elongate medical device 220 prior to distribution to the hospitals, clinic, or radiological imaging center. In such circumstances, the manufacturer of the elongate medical device 220 may bond the adapter tool 100 near a distal end 223 of the device 220 so that the adapter tool 100 is spaced apart from the distal 223 by a tip distance 110. In such embodiments, the tip distance 110 can be selected to have a sufficient length so that a distal tip region of the medical device 220 is exposed, thereby providing the practitioner with the options of using the medical device 220 with a hemostasis valves specifically configured to mate with the outer diameter of the distal end 223 (in which case the adapter tool 100 remains external to the hemostasis device) or using the medical device 220 with the hemostasis valve 200 that is configured to mate with a larger diameter device (in which case the adapter tool 100 is inserted into to the hemostasis device 200). Alternatively, the adapter tool 100 could being provided as a separate piece (e.g., apart from the medical device 220), and the practitioner can subsequently adhere or otherwise engage the adapter 100 to the exterior surface 222 of the medical device 220 after determining that inlet port 202 of the hemostasis valve 200 may not match perfectly with the exterior surface 222 of the medical device 220.

In the various embodiments in which the adapter tool 100 is used for securing the medical device 220 to the hemostasis valve device 200, the medical device 220 and adapter tool 100 are inserted into the inlet port 202 until the seal component 210 included in the inlet port 202 contacts the tapered body portion 112 (and preferably at least one protrusion 118 that extends outwardly from the tapered body portion 112). The adapter tool 100 and the inlet port 202 (e.g., including the seal component 210 or the inlet port 202) can engage to form a tight seal, and preferably a liquid tight seal, by manipulating the adapter tool 100 into secure contact inside the inlet port 202. For example, an adapter tool 100 can be press-fit or twist-fit into engagement so the hemostasis valve device 200 and the adapter 100 are secured in a relative position and thus remain stationary relative to one another during an intravascular procedure. In the embodiment depicted in FIG. 1, the adapter tool 100 and hemostasis valve device 200 are secured in the relative position so that a longitudinal axis 105 of the adapter tool 105 is generally axially aligned with a longitudinal axis 205 of the hemostasis valve device 200, thereby facilitating alignment of the access sheath 220 (or other elongate medical device) with the longitudinal axis 205 of the hemostasis valve device 200.

Still referring to FIGS. 1-2, the adapter tool 100 in this embodiment is configured to serve as a universal adapter for securing the medical device 220 to the hemostasis valve device 200. As such, the adapter tool 100 can be configured to fit a range of hemostasis valve devices. For example, the adapter tool 100 can be configured to fit hemostasis valve devices from a variety of manufacturers having a range of differently sized inlet ports included on such valve devices. The inlet ports can range in size and configuration based on manufacturer design. In particular, the inlet port may define an opening that is a predetermined size, e.g., a particular French size, but has a specific configuration that is proprietary to the manufacturer. The opening of the inlet port can be designed for a particular purpose, such as a type of procedure, or designed to accommodate a type of medical device. The adapter tool 100, however, can be mounted to the elongate medical device 220 so that it can be conveniently used with the hemostasis valve device intended for a different type or different size of medical device.

As shown in FIG. 1, the depicted example of the hemostasis valve device 200 may include an inlet port 202 with one or more seal components (e.g., inner seal component 210 and cap component 215 in this embodiment). The cap component 215 includes an opening 216 that allows the elongate medical device 220 to move into or out of the hemostasis valve 202. In this example, the opening 216 of the cap component 215 can comprises polyisoprene or silicone rubber material, which thereby provides a sealing engagement with the device (e.g., the adapter tool 100 in this embodiment) engaged with the wall of the opening 216. Additionally or alternatively, the inner seal component 210 can provide a flexible seal interface with the device (e.g., the adapter tool 100 in this embodiment) engaged with the component 210. Also, the inlet region of the hemostasis valve device 200 can be configured with different locking mechanisms, such as twist-locks or push-pull locks for locking the position of the adapter tool 100/medical device 220. It should be understood from the description herein that other embodiments of the hemostasis valve device 200 can employ other types of valve components to prevent blood drawback while permitting insertion/retraction of adapter tool 100 during a procedure.

As shown in FIG. 2, the adapter tool 100 can be used with a variety of medical devices, sheath-type medical devices, e.g., extenders, or other elongate medical devices that are used with a hemostasis valve. Example medical devices include catheters (including mini-catheters), probes, guide wires, lumen instruments, and other intravascular devices. Medical devices of this type can be inserted into a patient through the hemostasis valve device 200 or other device configured to offer hemostasis valve functionality. For example, an access sheath 220 (which can be used to advance one or more guide wires therethrough) is inserted into the hemostasis valve 202 during an intravascular procedure as illustrated in FIG. 1. In this way, a physician can insert or retract the guide wires into a vein or artery while maintaining a fluid seal.

Referring to FIG. 2, the adapter tool 100 can includes a body portion 112 with a generally tapered shape. For example, the tapered shape may be at least partially defined by a linear slope to provide a frustroconical shape. In another example, the tapered shape may be at least partially defined by a curved slope, such as a concave slope to provide a hyperbolic conical shape or a convex slope to provide a bulbous shape. The extent to which the body portion 112 tapers relative to the longitudinal axis 105 can be selected according to a number of factors. For example, the body portion 112 may have proportions (e.g., slope or length in comparison to its radius) based on the range of openings into which it may be inserted, internal fluid pressure, opening size, size of an expected medical device, expected sheath size, and so forth. For example, a body portion with a long length in comparison to the radius of its base may not secure as well in comparison to a body portion with a larger diameter end radius in comparison to its length.

The body portion 112 can be axially aligned with the longitudinal axis 105 of the adapter tool 105, which may extends through its center along its maximum length. In some embodiments, the axis 105 is generally perpendicular to the base radius of the body portion 112. Also, the body portion 112 may at least partially define a passage 116 that extends along the axis 105. For example, the passage 116 can be configured to accept different sized sheaths of other elongate medical instruments. In some embodiments, the interior wall 117 of the passage 116 can comprise a material (such as a flexible silicone) that is configured to deform slightly to accept a sheath device 220 while permitting the wall 117 of the passage 116 to form a tight seal around the sheath device 220, e.g., a fluid tight seal.

In some implementations described herein, the adapter tool 100 is adhesively connected to the sheath device 220 or other elongate medical device using, for example, a medical grade adhesive. The adhesive can form a seal (or supplement the seal) between the exterior surface 222 of the sheath device 220 and the wall 117 of the central passage 116. A manufacturer, wholesaler, retailer, or other intermediary may fixedly secure the adapter tool 116 to the medical device 220 so the medical device 220 can be provided as a unit, e.g., a prepackaged sterile unit (having the adapter tool 100 mounted thereon) that is ready for end use. Alternatively, the adapter tool 100 can be configured to slidably engage the sheath device 220 (free of any adhesive) during use. As previously described, the interior wall 117 of the passage 116 can comprise a material (such as a flexible silicone) that is configured to deform slightly in response to an insertion force of the sheath device 220 slidably advancing through the passage and that is configured to rest against and provide a frictional gripping force (and a sealing engagement) when the sheath device 220 comes to a stop within the passage 116.

Referring again to FIGS. 1-2, some embodiments of the adapter tool 100 include one or more protrusions 118 for engaging with a component of the inlet port 202 of the hemostasis valve device 200. The protrusions can be configured to engage with, for instance, a seal (e.g., inner seal component 210, the cap component 216, or the like) or a complaint wall that at least partially forms the inlet port in order to form a tight seal around the protrusion 118. It is to be appreciated that in addition to the protrusions 118, the sealing component(s) of the inlet port 202 can engage with, or at least partially engage with, a portion of the outer surface 120 of the body portion 112.

In some embodiments, the protrusions 118 extend outwardly from axis 105 and the outer surface 120 of the body portion. For example, the protrusions 118 may extend radially outward from the axis 105 of the tool 100. The body portion 112, the protrusions, or both can be symmetric about the axis 105 or about a longitudinal plane extending along the axis 105. As illustrated in the example in FIG. 2, each of the protrusions 118 is shaped as a ring that protrudes beyond a major portion of the outer surface 120 of the body portion 112. The protrusions 118 can have a variety of cross-sections (e.g., V-shaped, U-shaped), widths, and heights, depending on design preference, the range of hemostasis valves that it is to be used with, and other factors. Further, an adapter can include protrusions that have the same or different cross-sectional: shapes, widths, height, shapes, hardness, and the like. For example, a protrusion 118 forming a ring near a narrow distal end 122 of the tapered body portion 112 may have a smaller cross-section, a different height, and/or a different shape than that of a protrusion 118 that is adjacent a larger proximal end 124 of the tapered body portion 112.

In the embodiment depicted in FIG. 2, the protrusions 118 are axially aligned as annular rings of different diameters and axially spaced along the length of the body portion 112. In this configuration, the individual protrusions 118 can protrude to different extents from the axis 105 (e.g., have progressively increasing overall outer diameters), although individual protrusions may extend the same radial distance from the outer surface 120 of the body portion 112 (e.g., each ring protrusion 118 in this embodiment extends ⅛-inch from the outer surface 120). Accordingly, in such embodiments, a user can press-fit the adapter tool 100 into the inlet port 202 by pressing the adapter tool 100 (optionally, along with the medical device 220 mounted therein) inwardly towards the port 202 in a generally linear manner until one or more protrusions engage the corresponding seal component 210 of the port 202. For example, a user may press in the adapter tool 100 until the seal component 210 comes in contact with a protrusion 118 of a particular diameter, at which point, the adapter tool 100 is engaged so the seal component 210 deforms sufficiently to provide a sealing engagement around body portion 112.

In the embodiments in which the protrusions 118 are formed as rings, the individual rings 118 can be spaced at uniform distances along the length of the axis 105. Alternatively, the rings 118 may be non-uniformly spaced along the axis 105 (e.g., two or more rings may be clustered about an axial position) to afford slightly different diameters to account for manufacturing inconsistencies in the hemostasis valves, provide multiple contact points for engaging with the port, and so forth.

In addition to forming a liquid or pneumatically tight seal, the adapter tool 100 can be configured so it engages in a sufficiently tight manner to prevent the adapter tool 100 from inadvertently withdrawing from the hemostasis valve 200 during manipulation of the medical device 220. For example, the adapter tool 100 is configured to achieve a sufficiently snug fit so normal push-pull insertion or removal of the medical device 220 can be achieved without loosening the adapter tool 100 from the hemostasis valve device 200.

As shown in FIG. 2, the adapter tool 100 may optionally include a grasping portion 126 that is structured to facilitate finger or hand grasping such as for insertion or removal of the adapter tool 100 to or from the hemostasis valve device 200. In the illustrated embodiment, the grasping portion 126 is bounded by a pommel 128 that prevents or minimizes the likelihood of a user's fingers slipping when inserting the adapter in a press-fit manner. The contour of the grasping portion 126 may be selected to facilitate an insertion, engaging, or removal action. Also, in some embodiments, the grasping portion 126 has an axial length (along the axis 105) that is greater than an axial length of the body portion 112 (which carries the protrusions 118). The grasping portion 126 can be configured to press-fit the adapter tool 100 in a linear manner so it seats it in the port 202 or to facilitate a rotating or twisting action for threaded protrusions (described below). The grasping portion 126 can include texturing or include a surface treatment to facilitate manipulation, e.g., gloved manipulation. It is to be apparent that the grasping portion 126 may be formed of, or coated with a material to aid grasping. For example, a tacky outer layer (in comparison to other portions of the adapter) can be applied or co-formed in the grasping area.

The adapter tool 100 can be formed of a variety of biocompatible and sterilizable materials selected for performance characteristics. Characteristics include, but are not limited to, rigidity, deformability, resistance to degradation (thermal, radiation, water, light, electrical), inertness (e.g., chemically inert), resistance to contamination or microbial growth, out-gassing, and so forth. In embodiments, the adapter tool 100 is formed of a medical grade silicone or polyisobutylene, polyisoprene, or other medical grade plastic/rubber material, and copolymers thereof, and combinations thereof. In some instances, the material forming the body portion is loaded or impregnated with another material to give it a one or more physical, biological-related, or chemical properties. For example, the plastic for the body portion is infused with a radiation blocking to make resistant to x-ray that may be used in a medical procedure.

Also, each of the protrusions 118 can be formed of the same material as that of the body portion 112. Alternatively, each of the protrusions 118 can be formed of a different material as that of the body portion 112, in which case the protrusion may be co-molded with the body portion 112. Each of the protrusions 118 can be formed of a mix of materials to provide a variety of characteristics, such as: deformability, heat resistance, and so on. In some instances, a coating can be provided while the protrusions and/or body portion are formed of one or more other materials. For example, a polytetrafluroethylene, e.g., Teflon, outer surface may be formed as part of a blow-molding process.

Figure 3A:
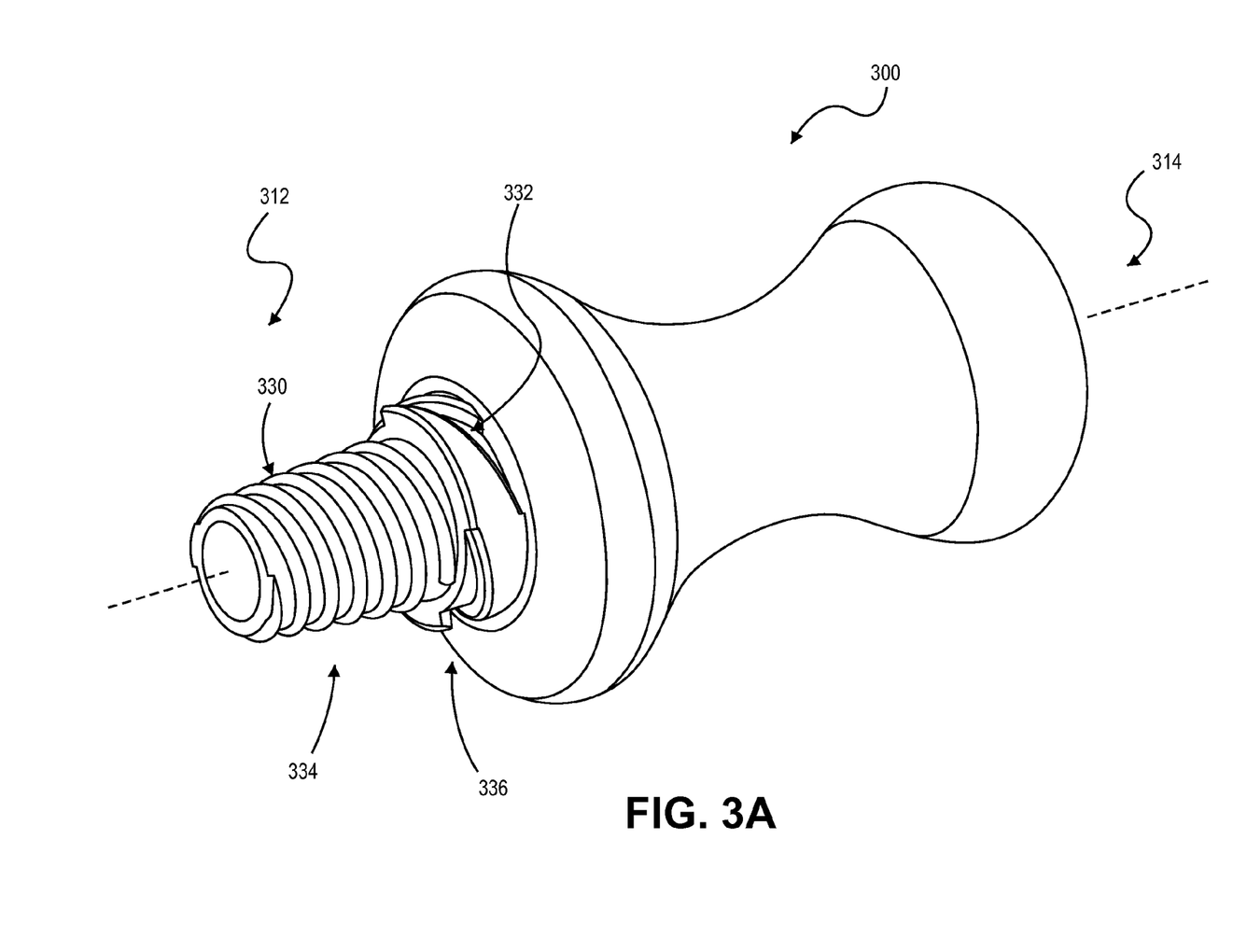
FIG. 3A is a perspective view of an adapter tool for securing a medical device to a valve instrument, in accordance with additional embodiments.

Referring now to FIG. 3A, some embodiments of an adapter tool 300 can include a protrusion configuration that is different from the adapter tool 100 illustrated in FIGS. 1-2. The adapter tool 300 in FIG. 3A can be similarly configured to secure an elongate medical device to an inlet port of a medical valve device (such as the hemostasis valve device 200). The adapter tool 300 can engage with elongate medical device 220 (FIG. 1) while also providing an effective seal with a valve component 210 (FIG. 1) even when the outer size of the elongate medical device 220 (FIG. 1) is not matched to the inlet port size of the valve device 200 (FIG. 1). As previously described, the adapter tool 300 can provide a transition between the inner valve component 210 (FIG. 1) of the hemostasis valve device 200 (FIG. 1) and the exterior surface 222 (FIG. 1) of the elongate medical device 220 (FIG. 1).

As shown in FIG. 3A, the adapter 300 includes at least one protrusion in the form of a thread along the tapered body portion 312. In this embodiment, a first protrusion 330 defines a first type of thread, and a second protrusion 332 defines a second type of thread. The threaded protrusions 330 and 332 are formed on different tapered regions 334 and 336, respectively, of the body portion 312. In other words, the first threaded protrusion 332 extends outwardly from the first tapered region 334 and the second threaded protrusion 336 extends outwardly from the second tapered region 336 to accommodate a larger sized port than that of the first tapered region 334. As previously described, the tapered shape of each portion 334 and 336 may be at least partially defined by a linear slope or a curved slope.

The protrusions 330, 332 provide a thread about the axis 305 of the adapter tool 300 to permit engagement by rotating or twisting the adapter tool 300 into a port. The pitch, the profile, and/or direction of the threaded protrusions 330, 332 can be selected based on a variety of factors including, selected seating compression, torque used to engage the threading with a port to ensure a tight seal, the protrusion's rigidity/deformation characteristics, resistance to forces applied during a medical procedure (e.g., push-pull action), and so on. The threaded protrusions 330, 332 may have similar or different characteristics. For example, the first threaded protrusion 330 may have a tighter pitch, have a narrower cross-section, and/or extend radially outward to a different extent in comparison to the second threaded protrusion.

The first protrusion 330 can have a pitch that twists in a first direction, e.g., clockwise. The second protrusion 332 can have a pitch that is opposite that of the first, e.g., twists in a counter-clockwise direction. The threaded protrusions 330, 332 can be configured to accommodate different sized and/or types of inlet ports. For example, the first threaded protrusion 330 is configured to work with a first size range of inlet ports while the second threaded protrusion 332 is configured to work with a second size range.

The first and second threaded protrusions 330, 332 can be configured so the adapter 300 may be inserted into a comparatively larger port without having to engage the smaller threaded protrusion, e.g., the first threaded protrusion 330, with the port. In this configuration, the adapter 300 is inserted into the port until the port engages with the second threaded protrusion 332 (the larger protrusion) where it can be secured by twisting the adapter 300. This allows the adapter 300 to be secured without having to engage the first threaded protrusion 330 (the smaller protrusion). In this configuration, the user does not have to have to reverse direction from, for example, clockwise to counter clockwise to engage the second threaded protrusion. Moreover, cross-threading can be avoided. These features may be accomplished by sizing the protrusions 330, 332 so the adapter 300 can be inserted linearly, thus bypassing the first threaded protrusion 330, before the second threaded protrusion 332 engages with the port. Configuring the adapter tool 300 in this manner, can minimize the rotation used to seal the adapter in a larger port, and/or permit the adapter to accommodate a larger size range of ports.

Figure 3B:
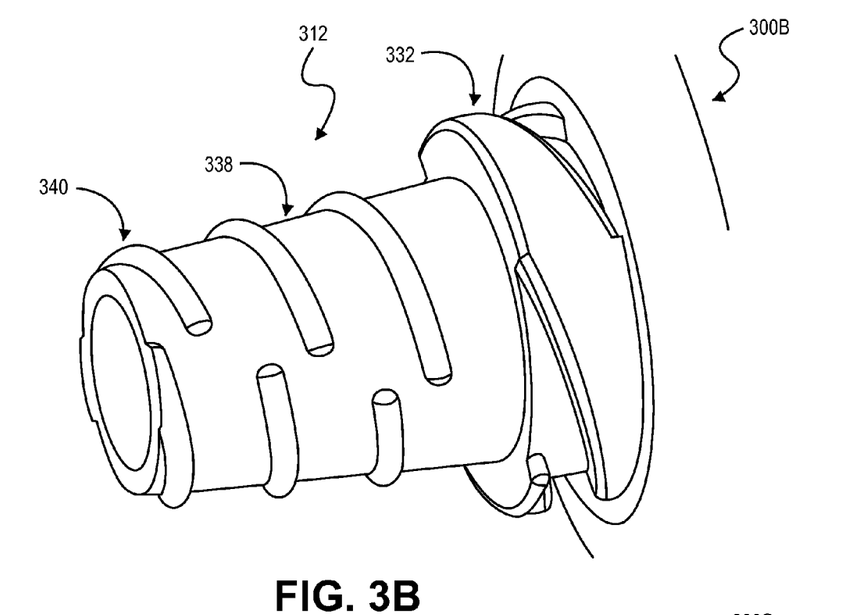
FIG. 3B is a perspective view of a portion of an adapter tool for securing a medical device to a valve instrument, in accordance with further embodiments.

Referring now to FIG. 3B, some embodiments of an adapter tool 300B can be equipped with threaded protrusions that are segmented. As illustrated, the threaded protrusions 340 are segmented so the protrusions 340 extend only partially around the circumference of the body portion 312, e.g., the protrusion is non-continuous about the outer surface 338. The protrusions 340 may be segmented to limit the rotation action that is used to engage with the port. For example, segmented protrusions 340 (one is referenced) can permit the adapter tool 300B to be linearly inserted into a port until a protrusion 340 contacts the port's seal component and then rotated to a limited extent, e.g., a quarter-turn is used to tighten the adapter tool 300B in the port. Constructing the adapter 300B in this way can increase convenience, use less material, and so forth. As illustrated, a second threaded protrusion 332, similar to that of FIG. 3A, can be optionally included along the tapered body portion 312.

Figure 3C:
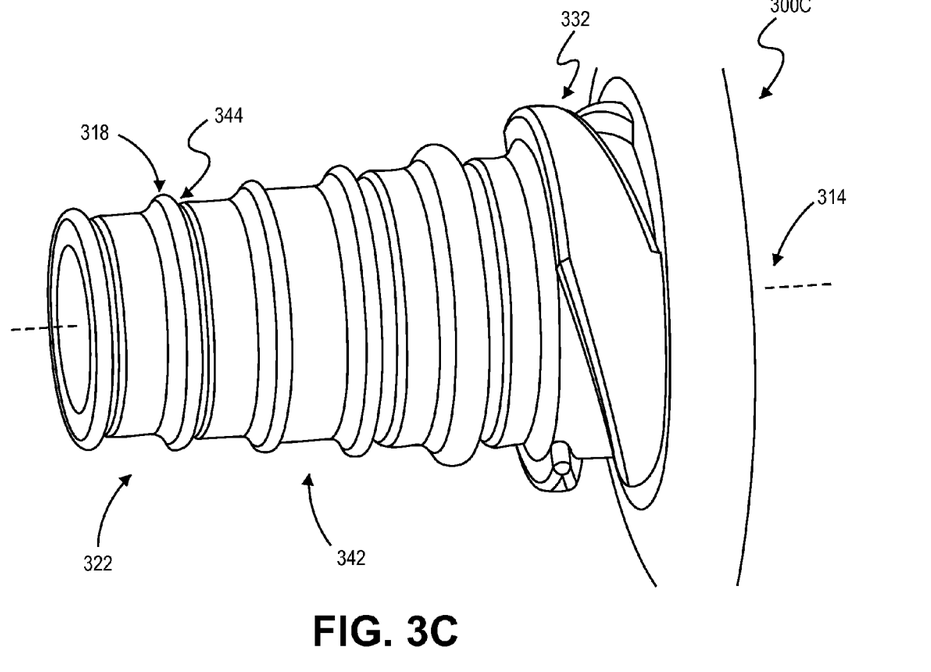
FIG. 3C is a perspective view of a portion of an adapter tool for securing a medical device to a valve instrument, in accordance with additional embodiments.

Referring now to FIG. 3C, some embodiments of an adapter tool 300C can be equipped with a combination of different protrusions. In this embodiment, a series of ring shaped protrusions 318 are included on a first tapered region 342 of the tapered body portion 312 and a threaded protrusion 332 is included of a second tapered region 346 so as to accommodate a larger sized port and/or for a port that more readily accepts a threaded protrusion. As can be seen, the ring protrusions 318 are substantially similar to those illustrated and described in conjunction with FIG. 2. As such, the adapter tool 300C can implement two different engagement modes based on port size, e.g., press-fit for narrower ports and twist-fit for larger ports.

Optionally, the individual ring protrusions 318 can be associated with a corresponding groove 344. For instance, a ring protrusion 318 has a corresponding groove 344 that is adjacent the ring 318 but farther along the axis 305 away from a distal end 322. In this configuration, a seal component (e.g., inner seal component 210) included on the inlet port 202 (FIG. 1) can snap over the ring protrusion 318 and at least partially seal within the surface of the groove 344 to form a tight seal. Movement of the adapter/valve seal along the adapter's axis toward the narrow end can be prevented by the engaged ring 318.

The following discussion describes methods that may be implemented in conjunction with the embodiments of the adapter tool described above. The techniques described below are independent of the structures described above, meaning that the techniques may be implemented in a variety of ways and are not necessarily limited to the structures illustrated in FIGS. 1-3C.

Figure 4:
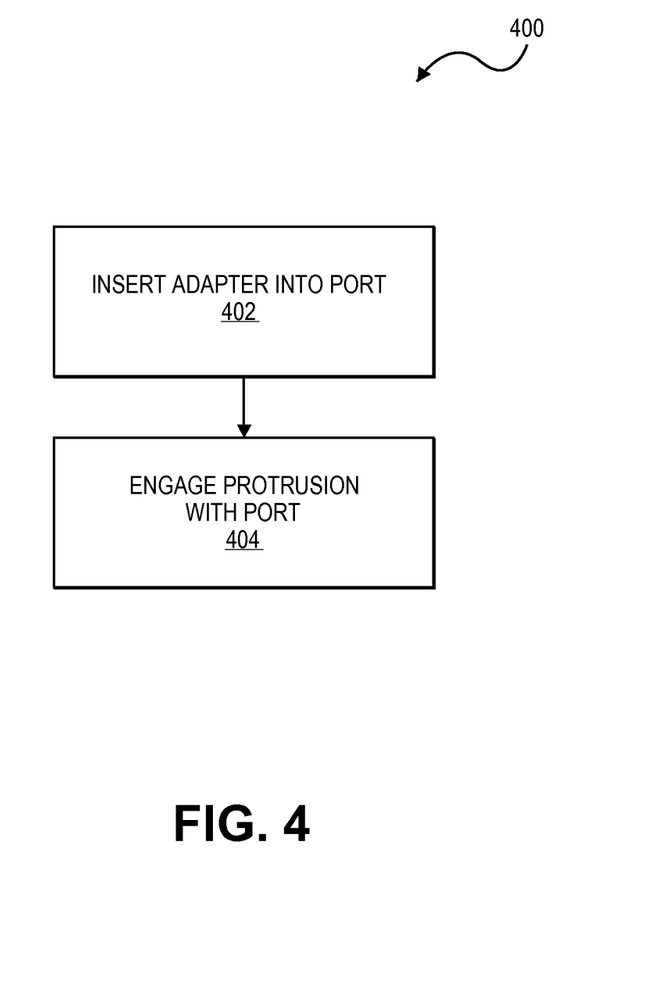
FIG. 4 is a flow diagram illustrating a method for securing a medical device with a valve instrument, such as a hemostasis, in accordance with some embodiments.

Referring to FIG. 4, some embodiments of a method 400 can use an adapter tool for securing a medical device to a hemostasis valve device. In some examples, the adapter tool 100, 300, 300B, or 300C can be used to provide a transition between the inner valve component of the hemostasis valve device and the exterior surface of the medical device. The method can be used to secure any of a variety of medical devices, such as those used in intravascular procedures.

Some embodiments of the method 400 may include operation 410, which comprises engaging a medical device within a passageway defined by an adapter tool. For example, a sheath 220 or other elongate medical device can be slidably or adhesive engaged within a passage 116 of the adapter tool 100 (FIGS. 1-2). As previously described, the medical device 220 can be engaged with the adapter tool prior to packaging the combination in a kit (e.g., preinstalled embodiments), or the medical device 220 can be engaged with the adapter tool 100 during the interventional procedure (e.g., at the hospital or clinic) after a practitioner determines that the medical device 200 may not fit perfectly with the inlet port 202 of the hemostasis valve.

Still referring to FIG. 4, the method 400 may also include the operation 420, which comprises installing a hemostasis valve in fluid communication with a blood vessel. For example, an outlet port of the hemostasis valve device 200 (FIG. 1) may be positioned in fluid communication with a vein or artery of a patient. Additionally, the method 400 may include operation 430 in which the adapter tool is inserted into an inlet port of the hemostasis valve. As previously described, the adapter tool 100 (FIG. 1) can be adhered or slidably engaged to an exterior surface 222 of the elongate medical device 220 to provide a sealed engagement therebetween. In those embodiment, the operation 430 would cause both the adapter tool 100 and the medical device 220 (FIG. 1) to be simultaneously inserted into the inlet port 202 (FIG. 1).

The method 400 may also include operation 440, in which at least one protrusion of the adapter tool is engaged with a seal component of the inlet port of the hemostasis valve device. For example, the adapter tool may be equipped with one or more protrusions on a tapered body portion (some example illustrated in FIGS. 2, 3A, 3B, and 3C), and at least one of the protrusions can be sized to engage with a seal component of the hemostasis valve device 200 (FIG. 1). As such, the adapter tool 100 can provide a transition between the valve component of the hemostasis valve device 200 and the exterior surface 222 of the elongate medical device 220 (FIG. 1). In some embodiments, a threaded protrusion that extends radially outward from an adapter tool can be rotated into engagement with a seal component of the inlet port to create a liquid tight seal. The liquid tight seal can be formed by applying sufficient torque on the adapter tool so the protrusion and/or at least a portion of the tapered body portion engages with the seal component so the adapter tool is seated in the inlet port. The seal between the inlet port and the adapter tool can be caused by the thread and/or the portion of the outer surface deforming as the adapter tool is rotated into engagement. Rotation may occur in a clockwise or counter-clockwise direction. The adapter's direction of rotation may depend on, for example, the size and/or configuration of the inlet port. In other embodiments, a ring-shaped protrusion along the adapter tool can be press-fit into engagement with the valve component, as previously described. Thus, a user can press the adapter tool into engagement so one or more of the rings engage with the hemostasis valve device.

The method 400 may optionally include operation 450 in which a fluid (e.g., medical fluid) or guide wire (or other elongate instrument) is advanced through the medical device engaged with the adapter tool. For example, as previously described, the medical device 220 (FIG. 1) can serve as an access sheath that permits a medical fluid, and imaging fluid, guide wires, or other instruments to advance through the medical device 220 and into the blood vessel coupled to the hemostasis valve device 200.

A number of embodiments of the invention have been described. Nevertheless, it will be understood that various modifications may be made without departing from the scope of the invention. Accordingly, other embodiments are within the scope of the following claims.

What is claimed is:

1. An adapter device for a medical device comprising:
   a generally tapered body portion configured to engage an inlet port of a hemostasis valve; and
   a grasping portion configured to be grasped during insertion of the generally tapered body portion into the inlet port of the hemostasis valve;
   the body portion defining a lumen to receive a medical device for passage of the medical device into the hemostasis valve;
   the body portion including one or more protrusions extending outwardly from a longitudinal axis of the body portion to sealingly engage with a component of the inlet port of the hemostasis valve, the one or more protrusions comprising a first threaded protrusion threaded in a clockwise direction and a second threaded protrusion threaded in a counter-clockwise direction.

2. The adapter device of claim 1, wherein the one or more protrusions comprise a series of annular ring protrusions having different outer diameters.

3. The adapter device of claim 1, wherein the one or more protrusions comprise at least one threaded protrusion that extends at least partially around an exterior of the generally tapered body portion so the threaded protrusion extends outwardly from the primary axis to different outer diameters along the threaded pitch of the protrusion.

4. The adapter device of claim 3, wherein the threaded protrusion extends continuously along a portion of the body portion.

5. The adapter device of claim 1, wherein the lumen extends longitudinally from a proximal-most end of the adapter device to a distal-most end of the adapter device.

6. The adapter device of claim 5, wherein the grasping portion is a contoured grasping portion joined to a proximal end of the generally tapered body portion, wherein the contoured grasping portion has a minimum exterior diameter in a central region of the contoured grasping portion that is smaller than both a diameter at a proximal end of the contoured grasping portion and a diameter at a distal end of the contoured grasping portion, the contoured grasping portion defining the proximal-most end of the adapter device and an input port at the proximal end of the lumen.

7. The adapter device of claim 6, wherein the generally tapered body portion has a constant interior diameter to define at least a portion of the lumen a longitudinal axis of the adapter device while an exterior diameter of the generally tapered body portion decreases toward the distal-most end of the adapter device, the generally tapered body portion defining the distal-most end of the adapter device and an output port at the distal end of the lumen.

8. The adapter device of claim 7, wherein the contoured grasping portion has a longitudinal length greater than a longitudinal length of the generally tapered body portion, a maximum exterior diameter greater than a maximum exterior diameter of the generally tapered body portion, and a minimum exterior diameter greater than a minimum exterior diameter of the generally tapered body portion.

9. The system of claim 1, wherein the lumen of the adapter tool extends longitudinally from a proximal-most end of the adapter tool to a distal-most end of the adapter tool.

10. The system of claim 9, wherein the grasping portion comprises a contoured grasping portion joined to a proximal end of the generally tapered body portion, wherein the contoured grasping portion has a minimum exterior diameter in a central region of the contoured grasping portion that is smaller than both a diameter at a proximal end of the contoured grasping portion and a diameter at a distal end of the contoured grasping portion, the contoured grasping portion defining the proximal-most end of the adapter device and an input port at the proximal end of the lumen.

11. The system of claim 10, wherein the generally tapered body portion of the adapter tool has a constant interior diameter to define at least a portion of the lumen a longitudinal axis of the adapter tool while an exterior diameter of the generally tapered body portion decreases toward the distal-most end of the adapter tool, the generally tapered body portion defining the distal-most end of the adapter tool and an output port at the distal end of the lumen.

12. The system of claim 11, wherein the contoured grasping portion of the adapter tool has a longitudinal length greater than a longitudinal length of the generally tapered body portion, a maximum exterior diameter greater than a maximum exterior diameter of the generally tapered body portion, and a minimum exterior diameter greater than a minimum exterior diameter of the generally tapered body portion.

13. An adapter device for a medical device comprising:
    a generally tapered body portion configured to engage an inlet port of a hemostasis valve;
    the body portion defining a lumen to receive a medical device for passage of the medical device into the hemostasis valve;
    the body portion including one or more protrusions extending outwardly from a longitudinal axis of the body portion to sealingly engage with a component of the inlet port of the hemostasis valve;
    wherein the one or more protrusions comprise a first threaded protrusion threaded in a clockwise direction and a second threaded protrusion threaded in a counter-clockwise direction, and at least one of the threaded protrusions extends at least partially around an exterior of the generally tapered body portion so the threaded protrusion extends outwardly from the primary axis to different outer diameters along the threaded pitch of the protrusion;
    wherein the at least one threaded protrusion extends continuously along a portion of the body portion.

14. The adapter device of claim 13, further comprising a grasping portion configured to be grasped during insertion of the generally tapered body portion into the inlet port of the hemostasis valve.

15. An adapter device for a medical device comprising:
    a generally tapered body portion configured to engage an inlet port of a hemostasis valve;
    the body portion defining a lumen to receive a medical device for passage of the medical device into the hemostasis valve;
    the body portion including one or more protrusions extending outwardly from a longitudinal axis of the body portion to sealingly engage with a component of the inlet port of the hemostasis valve;
    wherein the one or more protrusions comprise at least one threaded protrusion that extends at least partially around an exterior of the generally tapered body portion so the threaded protrusion extends outwardly from the primary axis to different outer diameters along the threaded pitch of the protrusion;
    wherein the one or more protrusions comprise a first threaded protrusion and a second threaded protrusion that, respectively, extend at least partially around the exterior of the generally tapered body portion, the first threaded protrusion being threaded in a clockwise direction and the second threaded protrusion being threaded in a counter-clockwise direction, the first and second threaded protrusions being located at different axial locations on the exterior of the generally tapered body portion along the primary axis.

16. The adapter device of claim 15, wherein at least one of the first or second protrusions is discontinuous along its length.

17. The adapter device of claim 15, wherein the first and second threaded protrusions have different pitches.

18. The adapter device of claim 15, wherein the adapter device is configured to permit engagement of the second threaded protrusion with the inlet port of the hemostasis valve without having to rotate the body portion in a direction opposite that used to thread the second threaded portion into engagement with the inlet port of the hemostasis valve.

19. The adapter device of claim 18, wherein the lumen defined by the body portion comprises a flexible material configured to comply in response to insertion of the medical device through the lumen and configured to provide a sealing engagement with an exterior surface of the medical device.

20. An system for securing a medical device to a medical valve instrument, comprising:
   a medical device having an elongate body and an exterior surface;
   an adapter tool defining a lumen along a longitudinal axis, the elongate body of the medical device being positioned with the lumen of the adapter tool so as to provide a sealed engagement between the adapter tool and the exterior surface of the medical device, wherein the adapter tool comprises:
      a generally tapered body portion configured to engage an inlet port of a hemostasis valve, the generally tapered body portion surrounding the lumen and the medical device therein, the generally tapered body portion including one or more protrusions extending outwardly from the longitudinal axis of the body portion to sealingly engage with a component of the inlet port of the hemostasis valve; and
      a grasping portion configured to be grasped during insertion of the generally tapered body portion into the inlet port of the hemostasis valve;
      wherein the one or more protrusions comprise a first threaded protrusion threaded in a clockwise direction and a second threaded protrusion threaded in a counter-clockwise direction.

21. The system of claim 20, wherein the one or more protrusions comprise a series of annular ring protrusions having different outer diameters.

22. The system of claim 20, wherein the one or more protrusions comprise at least one threaded protrusion that extends at least partially around an exterior of the generally tapered body portion so the threaded protrusion extends outwardly from the primary axis to different outer diameters along the threaded pitch of the protrusion.

23. The adapter device of claim 20, wherein the lumen defined by the body portion comprises a flexible material configured to comply in response to insertion of the medical device through the lumen and configured to provide a sealing engagement with the exterior surface of the medical device.

24. A universal hemostasis valve adapter for an extender, comprising:
   a generally tapered body portion defining a central passage configured to accept the extender for insertion into a hemostasis valve, the body portion including at least one radially extending protrusion disposed on a surface of the generally tapered body portion, the at least one radially extending protrusion configured to engage an entry port included on the hemostasis valve; and
   a grasping portion configured to be grasped during insertion of the generally tapered body portion into the inlet port of the hemostasis valve;
   wherein the at least one radially extending protrusion comprises a first threaded protrusion threaded in a clockwise direction and a second threaded protrusion threaded in a counter-clockwise direction.

25. The universal hemostasis valve adapter of claim 24, wherein the body portion has sufficient rigidity to retain its tapered shape, wherein the body portion is deformable to develop an at least partially liquid impervious seal with the entry port.

26. The universal hemostasis valve adapter of claim 24, wherein at least one of the threaded protrusions comprises a threaded protrusion that extends at least partially around the tapered surface so the threaded protrusion extends outwardly different extents along the threaded protrusion.

27. A universal hemostasis valve adapter for an extender, comprising:
   a generally tapered body portion defining a central passage configured to accept the extender for insertion into a hemostasis valve,
   the body portion including at least one radially extending protrusion disposed on a surface of the generally tapered body portion, the at least one radially extending protrusion configured to engage an entry port included on the hemostasis valve;
   wherein the at least one protrusion comprises a first threaded protrusion and a second threaded that, respectively, extend at least partially around the tapered surface, the first threaded protrusion being threaded in a clockwise direction and the second threaded protrusion being threaded in a counter-clockwise direction.

28. The universal hemostasis valve adapter of claim 27, wherein the adapter is configured to permit engagement of the second threaded protrusion with the entry port without having to rotate the body portion in a direction opposite that used to thread the second threaded portion into engagement with the entry port.

29. The universal hemostasis valve adapter of claim 27, wherein the first and second threaded protrusions have different pitches.

* * * * *

UNITED STATES PATENT AND TRADEMARK OFFICE
CERTIFICATE OF CORRECTION

PATENT NO. : 9,943,677 B2
APPLICATION NO. : 14/514815
DATED : April 17, 2018
INVENTOR(S) : Gregory Gordon et al.

It is certified that error appears in the above-identified patent and that said Letters Patent is hereby corrected as shown below:

In the Claims

Column 14, Line 63 (Approx.), In Claim 9, after "1" insert -- 20 --

Signed and Sealed this
Thirtieth Day of July, 2019

Andrei Iancu
*Director of the United States Patent and Trademark Office*